(12) United States Patent
Kaji et al.

(10) Patent No.: US 6,794,648 B2
(45) Date of Patent: Sep. 21, 2004

(54) ULTIMATE ANALYZER, SCANNING TRANSMISSION ELECTRON MICROSCOPE AND ULTIMATE ANALYSIS METHOD

(75) Inventors: Kazutoshi Kaji, Hitachi (JP); Takashi Aoyama, Tokai (JP); Shunroku Taya, Mito (JP); Hiroyuki Tanaka, Hitachinaka (JP); Shigeto Isakozawa, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 41 days.

(21) Appl. No.: 10/196,577

(22) Filed: Jul. 17, 2002

(65) Prior Publication Data

US 2003/0085356 A1 May 8, 2003

Related U.S. Application Data

(63) Continuation-in-part of application No. 10/069,793, filed as application No. PCT/JP01/09618 on Nov. 2, 2001.

(51) Int. Cl.[7] .......................... H01J 37/26; H01J 37/153
(52) U.S. Cl. ...................... 250/311; 250/305; 250/306; 250/310
(58) Field of Search ......................................... 250/311

(56) References Cited

U.S. PATENT DOCUMENTS

| | | | | |
|---|---|---|---|---|
| 4,743,756 A | * | 5/1988 | Krivanek | 250/305 |
| 6,531,697 B1 | * | 3/2003 | Nakamura et al. | 250/311 |

FOREIGN PATENT DOCUMENTS

| | | |
|---|---|---|
| JP | 57-80649 | 5/1982 |
| JP | 61-014552 | 1/1986 |
| JP | 7-21966 | 1/1995 |
| JP | 7-21967 | 1/1995 |
| JP | 7-29544 | 1/1995 |
| JP | 2000-021346 | 1/2000 |
| JP | 2001-153820 | 6/2001 |
| JP | 2001-307672 | 11/2001 |

OTHER PUBLICATIONS

Takahito (Patent Abstracts of Japan, publication No. 200-021346).*

* cited by examiner

Primary Examiner—John R. Lee
Assistant Examiner—James J. Leybourne
(74) Attorney, Agent, or Firm—Dickstein Shapiro Morin & Oshinsky LLP

(57) ABSTRACT

An object of the present invention is to provide an ultimate analyzer which can display an element distribution image of an object to be analyzed with high contrast to determine the positions of the element distribution with high accuracy, and a scanning transmission electron microscope and a method of analyzing elements using the ultimate analyzer. The present invention exists in an ultimate analyzer comprising a scattered electron beam detector for detecting an electron beam scattered by an object to be analyzed; an electron spectrometer for energy dispersing an electron beam transmitted through the object to be analyzed; an electron beam detector for detecting said dispersed electron beam; and a control unit for analyzing elements of the object to be analyzed based on an output signal of the electron beam detected by the electron beam detector and an output signal of the electron beam detected by the scattered electron beam detector. Further, the present invention exists in a scanning transmission electron microscope comprising the above ultimate analyzer; an electron beam source; an electron beam scanning coil; a scattered electron beam detector; objective lenses; a focusing lens; a magnifying magnetic field lens; and a focus adjusting electromagnetic lens. Furthermore, the ultimate analyzer or the scanning transmission electron microscope may comprises a control unit which makes it possible that both of an image of element distribution and an STEM image detected and formed by the scatted electron beam detector are observed at a time in real time, and the image of element distribution is corrected by the STEM image detected and formed by the scattered electron beam detector.

19 Claims, 5 Drawing Sheets

ULTIMATE ANALYZER, SCANNING TRANSMISSION ELECTRON MICROSCOPE AND ULTIMATE ANALYSIS METHOD

This is a continuation-in-part of U.S. patent application Ser. No. 10/069,793, filed Apr. 3, 2002 which is a 371 of Application No. PCT/JP01/09618 on Nov. 2, 2001, the entire disclosure of which is incorporated herein by reference.

BACKGROUND OF THE INVENTION

The present invention relates to a novel ultimate analyzer for analyzing elements of an object to be analyzed based on an output signal of a scattered electron beam and a plurality of output signals of an electron beam energy dispersed after passing through an object to be analyzed, and a scanning transmission electron microscope having the ultimate analyzer and an ultimate analysis method using the scanning transmission electron microscope.

With progressing of miniaturizing and downsizing of semiconductor devices and magnetic head elements, the structure of these elements has a structure that thin films of several nm (nanometers) are laminated in an area of a sub-micrometer order. Since the characteristics of the semiconductor elements and the magnetic head elements strongly depend on the structure, the element distribution and the crystal structure in such a micro-area, it is important to analyze them in the micro-area.

As the means for observing a micro-area, there are a scanning electron microscope (SEM), a transmission electron microscope (TEM) and a scanning transmission electron microscope (STEM). Only the TEM and the STEM have a spatial resolution of a nanometer level. The TEM is an apparatus in which an electron beam is irradiated onto a sample, and the transmitted electron beam is magnified using a lens. On the other hand, the STEM is an apparatus in which an electron beam is focused onto a micro-area, and a two-dimensional image is obtained by measuring intensities of the transmitted electron beam while the electron beam is being scanned on the sample.

As the means for observing a two-dimensional distribution of elements on a plane of a sample, there are an energy dispersive X-ray spectroscopy (EDX) and an electron energy loss spectroscopy (EELS) using the TEM or the STEM. For example, in a case of analyzing a metal film, Cr, Mn, Fe, Co, Ni and Cu can be identified using the energy dispersive X-ray spectroscopy, and two-dimensional distributions of the above metals can be obtained.

On the other hand, by using the electron energy loss spectroscopy, silicon, oxygen and nitrogen can be identified, and two-dimensional distributions of silicon, silicon oxide and silicon nitride can be observed. The electron energy loss spectroscopy is a method of analyzing lost energy for exciting inner-shell electrons of elements composing a sample when the electron beam transmitting through the sample. The electron that lost energy due to the excitation of the inner-shell of the element to be analyzed is called as core-loss electron. The ultimate analysis can be performed because the lost energy is specific to an element, and a two-dimensional distribution of the elements can be observed by performing energy analysis in each position in the plane of the sample. These spectroscopy are widely used by combining the STEM and a parallel detection type electron beam energy loss spectrometer.

The parallel detection type electron beam energy loss spectrometer comprises a magnetic-prism spectrometer; quadrupole electromagnetic lenses and hexapole electromagnetic lenses arranged at the front of and at the rear of the magnetic-prism spectrometer; and a parallel detector arranged after the magnetic-prism spectrometer. The quadrupole electromagnetic lenses are used for adjusting focus of the electron energy loss spectra and for magnifying the electron energy loss spectra. The hexapole electromagnetic lens is used for reducing aberration of the electron energy loss spectra projected on the detector. The electron energy loss spectra magnified by the quadrupole electromagnetic lens is projected on the parallel detector to measure a wide range of the electron energy loss spectra.

The prior art in regard to the structure of the parallel detection type electron energy loss spectrometer is disclosed in, for example, U.S. Pat. No. 4,743,756, Japanese Patent Application Laid-Open No. 7-21966, Japanese Patent Application Laid-Open No. 7-21967, and Japanese Patent Application Laid-Open No. 7-29544. An electron energy analyzer is disclosed in Japanese Patent Application Laid-Open No. 57-80649.

In a conventional apparatus combining the parallel detection type electron energy loss spectrometer and the STEM, a user performs (1) specifying a measured position, (2) specifying an element, (3) measuring an energy intensity distribution of the electron beam using the electron beam detection part, (4) correcting background of the detection part and correcting the gain of the detection part, (5) specifying a background region of the spectrum, (6) specifying a background fitting function such as the power-low model (I=A×E$^{-r}$; A and r are coefficients, and E is energy), (7) specifying an integration region of the signal intensity, (8) displaying the signal intensity of the specified element in the measured position on the image display unit, and (9) performing the operation of the item (1). Since it is necessary to perform the repetitive operation described above for all the measuring points, it takes a long time to obtain a two-dimensional image, and accordingly it is difficult to obtain an element distribution in real time. Further, it can be considered to obtain the two-dimensional image by the method that after measuring the electron energy loss spectra for all the measured points, the user specifies the operations of (2) to (7). In this method, the volume of measured data becomes very large, and further, the element distribution image can not be obtained in real time.

In addition to the above, in the case where the element distribution image can not be obtained in real time, there are following problems:

(A) In a case where analysis of an interface between thin films, the analysis region (the interface between thin films) can not be identified by using a TEM/STEM image when measuring the electron energy loss spectra. Accordingly, whether or not the region to be measured is included in the analyzed region cannot be judged until the element distribution image is obtained after analyzing the electron energy loss spectra.

(B) The conventional analyzer is not suitable for the work such as the inspection to measure many samples because it requires the measurement of the electron energy loss spectra and the many complicated and complex operations for each measured point, and also it requires a long time for the measurement and the analysis.

(C) In a case of identifying an oxide film or a deposited element formed in an interface between dissimilar metals, it cannot be identified by observing only a distribution image of the single element which metal between the dissimilar metals is oxidized, or it is difficult to be identified by observing the element distribution image whether the elements exist on the interface between the dissimilar metals or are distributed inside one of the metals.

Further, in an analyzer which detects an element to be analyzed by dividing an intensity of a first electron beam in an energy range containing a core-loss peak among the electron energy loss spectra of the element to be measured by an intensity of a second electron beam in an energy range higher than the core-loss peak, which is called as a jump-ratio method, there is the following problem depending on the sample to be analyzed.

When light elements such as oxygen, nitrogen and the like are observed in a case where a heavy metal element exists in the sample to be measured, a portion of the heavy metal element is sometimes displayed with brightness similar to brightness of the distribution image of the light elements. In that case, since the contrast difference between a metal portion and an oxide or nitride portion becomes small, it becomes difficult to judge correctly existence of oxide or nitride.

As described above, the analyzer combining the electron energy loss spectrometer and the STEM is difficult to observe an element distribution image having high contrast in real time and to determine the distribution of the element with high accuracy.

On the other hand, as a means for preventing degradation of an image due to brightness variation of an electron source in STEM image observation using a scanning transmission electron microscope, Japanese Patent Application Laid-Open No. 2000-21346 discloses a scanning transmission electron microscope in which one of an output signal from a detecting means for detecting transmission electrons transmitted through a sample and an output signal from a detecting means for detecting scattered electrons scattered by the sample is divided by the other. However, this patent discloses a means for improving image quality of a STEM image, but not a means for analyzing elements of the sample.

The literature by K. Kaji, et al., "Light Element Mapping Method with Scanning Transmission Electron Microscope", *The Japanese Society of Electron Microscopy*, May 17, 2000: p307, describes a method for obtaining an oxygen distribution image, in which gate electrodes are dark and oxidized films thereon are bright.

According to the description, using a transmission electron scanning microscope of a field-emission type and an ultimate analyzing observation apparatus, the method obtains such image by logical dividing operation applied to an oxygen distribution image acquired by 2-window method using a Z-contrast image as the divisor.

However, this method is still not enough to respond to the demand for more contrasted screen-displaying of gate electrodes and oxidized films thereon.

BRIEF SUMMARY OF THE INVENTION

An object of the present invention is to provide an ultimate analyzer which can display an element distribution image of an object to be analyzed with high contrast to determine the positions of the element distribution with high accuracy, and a scanning transmission electron microscope and a method of analyzing elements using the ultimate analyzer.

The present invention is characterized by an ultimate analyzer comprising a control unit for detecting an element of an object to be analyzed based on an output signal of an electron beam detector by dispersing an electron beam transmitted through a sample, particularly, based on an intensity of the output signal and an output signal of a ring-shaped scatted electron beam detector for detecting an electron beam scattered by the sample.

Further, the present invention is characterized by an ultimate analyzer comprising an image display unit for displaying an element distribution image of an object to be analyzed obtained based on an intensity of an electron beam detected by an electron detector passing through a sample and being dispersed; and an element distribution image of the object to be analyzed obtained based on an intensity of an electron beam detected by the scattered electron beam detector described above.

Further, the present invention is characterized by an ultimate analyzer comprising any one of an image display unit for displaying line profiles of an element of the object to be analyzed obtained from an analysis result output from a control unit for analyzing the element of the object to be analyzed based on an intensity of the dispersed electron beam detected by the electron beam detector and an analysis result output from the control unit for analyzing the element of the object to be analyzed based on an intensity of the electron beam detected by the scattered electron beam detector, and an image display for displaying a distribution image of the element, and an image display unit for displaying the distribution image of the element and a distribution image of the element based on the intensity of the electron beam detected by the scattered electron beam detector with two image planes side-by-side at a time or with sequential one-image planes or with two image planes overlapped with each other. The output signal detected by the electron beam detector is expressed by the intensity, but the electron beam detector detects an amount of electrons.

Further, the present invention is characterized by a scanning transmission electron microscope comprising an electron beam source for generating an electron beam; an electron beam scanning coil; a scattered electron beam detector for detecting a scattered electron beam scattered by an object to be analyzed; an objective lens for condensing the electron beam on the object to be analyzed; a focusing lens; a magnifying magnetic field lens; a focus adjusting electromagnetic lens; a scanning portion for scanning the electron beam; an electron dispersing portion for energy-dispersing the electron beam; and an electron beam detector portion for detecting part or all of the electron beam energy-dispersed by the electron dispersing portion, which comprises the ultimate analyzer described above.

That is, the present invention is characterized by a scanning transmission electron microscope comprising a processor for performing operation using only an intensity of an electron beam detected by the electron beam detector for detecting at least part of the electron beam dispersed by the electron dispersing portion or using both of the intensity of the electron beam and a result of an intensity of an electron beam detected by the scattered electron beam detector, and displays the operated result of the processor at the same time or in parallel with scanning the electron beam using the scanning portion or after the electron beam scanning. Further, the present invention is characterized by that an image based on the electron beam intensity detected by the scattered electron beam detecting portion is displayed together with the operated result of the processor side-by-side or overlapping with each other. Therefore, by the analyzer combining an electron energy loss spectrometer and an STEM, an element distribution image can be displayed on a screen in real time.

Further, the present invention is characterized by a scanning transmission electron microscope comprising the dispersing conditions of the electron beam losing energy due to the excitation of the inner-shell electron in the element to be analyzed; and two or more channels of electron beam detecting portions for detecting dispersed electron beams, wherein the ultimate analysis is progressed by specifying a element to be observed after specifying a measurement region; then obtaining energy dispersing conditions of coreloss electrons of the specified element from a dispersing condition memory unit; automatically adjusting the electron optical system of the electron dispersing portion and the electron beam detecting portion so that the core-loss electrons may be detected; measuring an intensity of the coreloss electrons and an intensity of electrons just lower than the energy of core-loss electrons by the electron beam detecting portion using at least one channel for each while the electron beam is being scanned using the scanning portion; performing background correction and gain correction of the electron beam detecting portion using the processor; executing operation, preferably, dividing an intensity of an electron beam of the core-loss edge in an electron energy loss spectrum by the intensity of an electron beam just before the core-loss edge; and displaying both of the operated result obtained by the division and the result based on the intensity of the electron beam detected by the scattered electron beam detector on the image display unit at a time or in parallel or overlapped with each other in real time.

Further, the scanning transmission electron microscope in accordance with the present invention is characterized by that the operated result obtained by dividing the intensity of an electron beam including core-loss electrons by the intensity of an electron beam whose energy is smaller than the energy of core-loss electrons is operated using the intensity of the electron beam detected by the scattered electron beam detecting portion, and the operated result obtained as the result is displayed solely or together with side-by-side or overlapped with an image based on the intensity of the electron beam detected by the scattered electron beam detecting portion on the image display unit in real time. When an image is formed by electrons scattered by a sample in a high angle using the scattered electron beam detecting portion, the obtained image is also called as a Z-contrast image.

The present invention is characterized by an ultimate analyzer which can observe and display an element distribution image and a Z-contrast image at a time in real time during scanning the electron beam, and can observe an element distribution image corrected by the Z-contrast image.

The present invention is characterized by an ultimate analysis method comprising the steps of detecting an output signal of an electron beam penetrated through an object to be analyzed, preferably as an intensity for each energy of the electron beam; and analyzing an element, preferably a non-metallic element, of the object to be analyzed based on an output signal of the detected electron beam, wherein the intensity of the output signal is corrected by an output signal, preferably by an intensity, of the electron beam scattered by the object to be analyzed.

Further, the present invention is characterized by that in the electron energy loss spectrum obtained by dispersing energy of an electron beam penetrated through an object to be analyzed, analysis of element of the object to be analyzed obtained by operating based on both an intensity of an electron beam within an energy range including a core-loss edge appearing in the electron energy loss spectrum by electrons exciting the inner-shell electron of an element composing the object to be analyzed and an intensity of an electron beam having a higher energy than the core-loss edge or the element analysis image are obtained by correcting the intensity of the electron beam scattered by the object to be analyzed.

Further, the present invention is characterized by that in an ultimate analysis method comprising the steps of detecting an intensity of an electron beam penetrated through an object to be analyzed; analyzing an element of the object to be analyzed based on the intensity and loss-energy of the detected electron beam; and displaying an image of the ultimate analysis on a screen, wherein the image of the ultimate analysis is displayed on the screen by being corrected by a Z-contrast image obtained from operation based on an intensity of an electron beam scattered by the object to be analyzed.

The present invention is to provide an ultimate analyzer comprising: a control unit for analyzing elements of said object to be analyzed based on a computed output signal obtained either through adding or subtracting operation applied between an intensity of a transmitted electron beam and an intensity of a scattered electron beam or through dividing operation applied to said transmitted beam intensity using the square root of said scattered beam intensity as the divisor; and a computing unit either for adding or subtracting operation between the intensity of said transmission electron beam and the intensity of said scattered electron beam or for dividing operation to said transmission beam intensity using the square root of said scattered electron beam intensity as the divisor; and a screen-display device for the corrected image of the analyzed results.

Another feature of the present invention is to provide a method for ultimate analysis comprising the steps of: correcting an image based on a computed output signal obtained either through adding or subtracting operation applied between an intensity of a transmitted electron beam and an intensity of a scattered electron beam or through dividing operation applied to said transmitted beam intensity using the square root of said scattered beam intensity as the divisor; and displaying the corrected image on a screen.

Said ultimate analysis image and a Z-contrast image may be displayed in any of styles: a side-by-side shared-screen assignment for said analysis image and said Z-contrast image, another side-by-side shared-screen assignment for said Z-contrast image and a processed image obtained by logically dividing said analysis image by said Z-contrast image, a switching display wherein said analysis image or said Z-contrast image appears by switching, or superimposed display of said ultimate analysis image and said Z-contrast image each being given contrast gradation with colors other than black and white but different each other.

On every electron beam position irradiated onto a specimen, the ultimate analysis result obtained through EELS spectrum or the same but obtained through EELS spectrum and said Z-contrast image is displayed. This means that the line profile is displayed.

DESCRIPTION OF THE PREFERRED EMBODIMENTS

Figure 1:
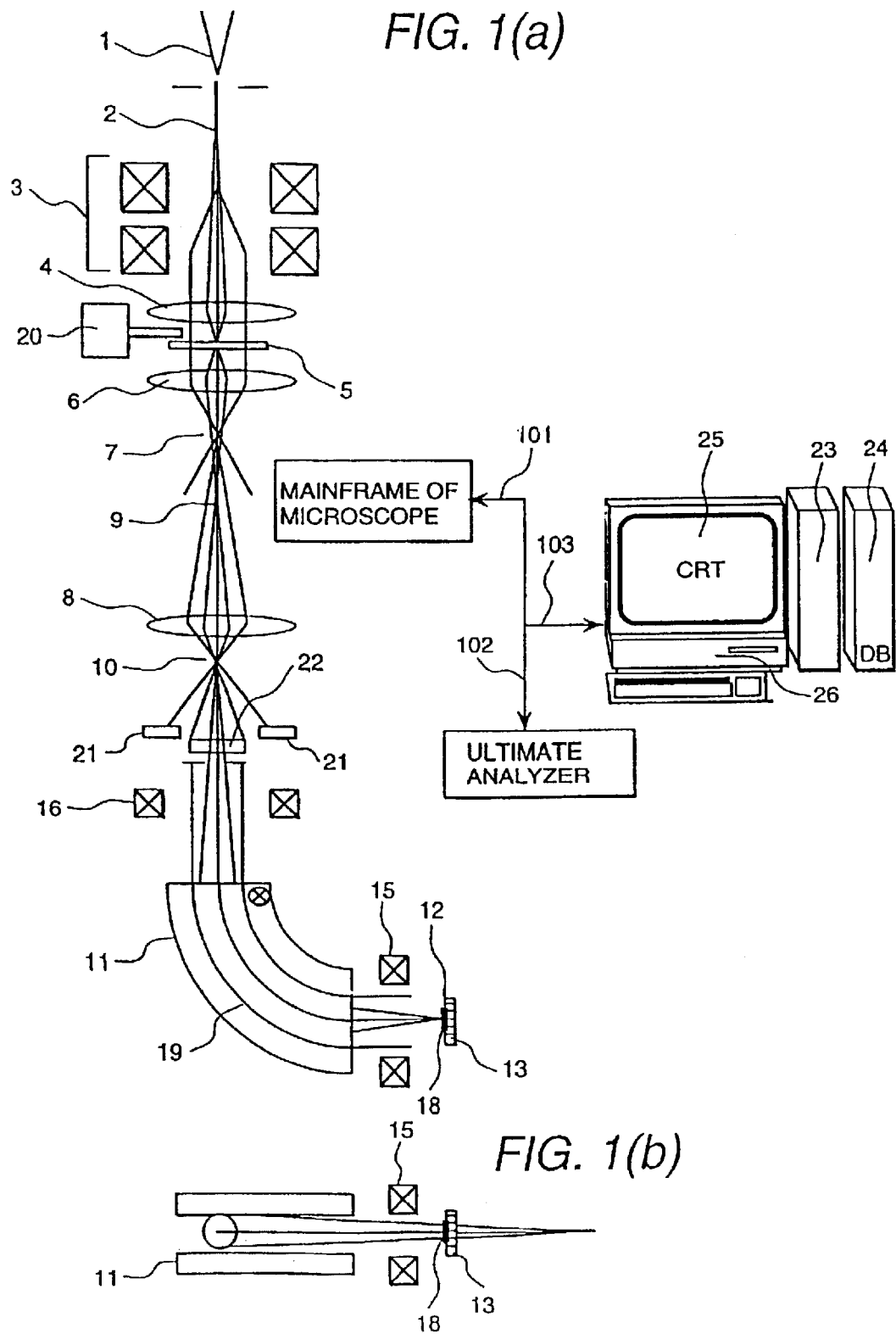
FIGS. 1(a) and (b) are schematic block diagrams showing the main portion of a scanning transmission electron microscope having an ultimate analyzer in accordance with the present invention.

FIG. 1 is a schematic block diagram showing the main portion of a scanning transmission electron microscope (hereinafter, referred to as an electron microscope) having an embodiment of an ultimate analyzer in accordance with the present invention. FIG. 1(a) is a front view, and FIG. 1(b) is a view (a top view) seeing FIG. 1(a) from an electron beam source 1. In this figure, the portion from the electron beam source 1 to a phase contrast detector 22 is indicated as the mainframe of the electron microscope. The mainframe of the electron microscope includes a component for controlling scanning of an electron beam, not shown, used for exerting the function as the electron microscope.

Further, the portion from a scattered electron beam detector 21 to an electron beam detector 13 is indicated by an ultimate analyzer. A signal to a control unit 26 and a signal from the control unit 26 are transmitted through a signal line 103. An input unit such as a keyboard and so on and a processor 23, a memory unit 24, and an image display unit 25 are connected to the control unit 26. A dispersing condition of Core-loss edge and plasmon energy for an element are stored in the memory unit 24. On the image display unit 25, an intensity of the electron beam detected by a secondary electron detector 20 and/or an intensity of the electron beam detected by the scattered electron detector 21 or a operated result of the processor 23 and a element to be analyzed specifying button capable of specifying two or more kinds of elements to be analyzed while the electron beam is being scanned are displayed.

The scattered electron beam detector 21 is of a ring-shape having a desired diameter, and detects the electron beam scattered by an element composing a semiconductor device or a magnetic head element by the whole circumference of the ring. Thereby, the scattered electron beam detector can detect the element with a high accuracy, and in order to appropriately detect the scattered electron beam, the intensity of the incident electron beam is controlled so that the scattered electron beam matches the diameter of the detector. Further, in order to form a high contrast image display, it is preferable to detect an element corresponding to an element to be displayed by arranging a plurality of scattered electron beam detectors 21 in the vertical direction or the transverse direction, as to be described later.

The electron beam 2 generated in the electron beam source 1 is deflected by an electron beam scanning coil 3. The deflected electron beam 2 is converted on the plane of a sample 5 by upper magnetic field 4 of an objective lens to be irradiated on the sample 5. Secondary electrons emitted from the sample are detected by a secondary electron detector 20, and the intensity of the detected electron beam is displayed on the image display unit 25 to observe the secondary electron image. Electrons scattered with a high angle among the electrons scattered by the sample are detected by a scattered electron beam detector 21, and the intensity of the detected electron beam is displayed on the image display unit 25 to observe the Z-contrast image.

The electron beam scattered by and transmitted through the sample forms an object point 10 by an objective lens lower magnetic field 6 and a projective lens 8. The electron beam having the object point 10 is incident to the ultimate analyzer. A spectrial electron spectrograph 11 arranged in the downstream side through a phase contrast detector 22 before a focus adjusting electromagnetic lens 16. The magnetic field of a magnet composing the magnetic-prism spectrometer 11 forms a magnetic field vertical to the plane of paper of FIG. 1. The electron beam incident to the magnetic-prism spectrometer 11 is deflected by 90° and energy-dispersed, and then focused on an energy dispersed plane 12. By adjusting the relationship between an output signal obtained by the scattered electron beam detector 21 and an output signal obtained by the electron beam detector 13 using a value obtained by the phase contrast detector 22, a high contrast can be formed.

In this embodiment, the spectrum formed on the energy dispersed plane 12 is about 1 eV/μm when the radius of rotation of the electron beam of the magnetic-prism spectrometer is 100 mm. In order to make the focus the spectrum magnified by the magnifying magnetic field lens 15 on the energy dispersing plane 12, the magnetic field of the focus adjusting electromagnetic lens 16 is adjusted. By doing so, the electron energy loss spectrum 18 projected on the electron beam detector 13 becomes 0.01 eV/μm. It becomes 0.25 eV/channel when a multi-channel plate array of 25 μm/channel is used as the electron beam detector 13. Since the detector is formed of 1024 channels, the full range becomes 250 eV.

Further, the electron beam detector 13 may have a structure that a plurality of scintillators having, for example, 2 mm channel width are arrayed in the energy dispersing direction, and light from the scintillators is amplified using a photomultiplier.

A real-time element mapping method using the present embodiment will be described below.

A user should be involved only in (1) a process to specify element, (2) a spectrum checking process and (3) an analysis region specifying process of processing to specify a measurement region. The other processes are executed under control of the control unit 26 to control the electron microscope mainframe and the ultimate analyzer.

The ultimate analyzer is constructed so that the zero loss electron beam comes near the center of the electron beam detector 13. The intensity of the electron beam lost above 250 eV as a result of the excitation of the inner-shell electron is measured by accelerating the electron beam using an accelerating tube 19 arranged inside the magnetic-prism spectrometer 11. When the intensity of the electron beam lost above 500 eV is measured, the loss electrons are accelerated by applying 500 V to the accelerating tube. By doing so, the loss electron beam required to be measured can be shifted to the center of the detector 13.

An element to be analyzed is displayed by buttons each having a name of element on the image display unit 25. When an element to be analyzed is specified using the element specifying button, a dispersing condition of the specified element is obtained from the dispersing condition memory unit 24, and the optical system is adjusted using the magnetic-prism spectrometer 11 of the ultimate analyzer and the accelerating tube 19 arranged in the magnetic-prism spectrometer, the magnification magnetic field lens 15, the focus adjusting magnetic field lens 16 and so on to perform element mapping. Further, by performing the above-described operation during scanning the electron beam, it is possible to perform mapping of two or more kinds of elements in real time by switching the element to be analyzed. The various kinds of images measured as described above are displayed on the image display unit 25.

Figure 2:
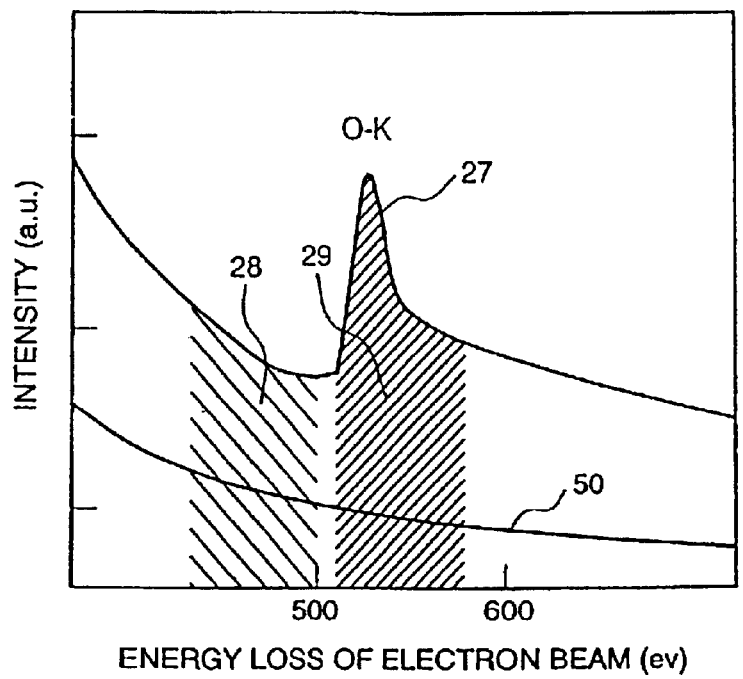
FIG. 2 is a graph showing an example of an electron beam energy loss spectrum of the core-loss electrons.

FIG. 2 is a graph showing a shape of an electron beam energy loss spectrum obtained by exciting inner-shell electrons of an element composing an object to be measured. When an electron beam is incident to a sample, electrons among the incident electrons lose energy specific to an element of the sample by exciting the inner-shell electron of the atom. The inner-shell electron exciting electron means the electron list its energy. As shown in FIG. 2(a), in a case where a spectrum showing the core-loss edge is measured by individually setting a range just before the core-loss edge 27 (pre-window 28) and a range including the core-loss edge (post-window 29) as one window, respectively, (2-window method), it is necessary to determine an energy width of the window and an energy width between the two windows. In the present embodiment, the operation is automated by storing the relating information in the memory unit 24.

The memory unit 24 stores the core-loss edge energy (eV), conditions of window width (energy width, or number of channels) and gap between windows (energy width, or number of channels), condition of the focus adjusting magnetic field lens 16, and condition of the magnifying magnetic field lens 15 for each element. When a user specifies an element to be analyzed, a voltage corresponding to the core-loss edge energy is applied to the acceleration tube 19, and an optimum current is conducted to each of the focus adjusting magnetic field lens 16 and the magnifying magnetic field lens 15, and a window width and a window gap are given by the memory unit 24. The electron beam intensities obtained from the two windows are corrected their backgrounds and gains specific to the detector in the processor 23, and then the intensity ratio of the two windows is operated and displayed on the image display unit 25. In this case, by outputting the control signal 101 from the control unit 26 to the electron microscope mainframe through the signal line 103 to performing the processing linking with the electron beam scanning coil 3, an element distribution image can be obtained in real time. By this method, the element distribution image can be obtained in a short processing time.

In the case of the two-window method, for example, in the electron energy loss spectrum 27 caused by the excitation of oxygen K-shell electron shown in FIG. 2, an oxygen distribution image can be obtained by dividing the electron beam intensity of the post-window 29 by the electron beam intensity of the pre-window 28. An electron energy loss spectrum 50 for a metal element is also shown in FIG. 2. However, when the electron beam intensity of the post-window 29 is divided by the electron beam intensity of the pre-window 28 in a case where the gradient of the electron energy loss spectrum 50 is small, the divided result sometimes becomes nearly equal to a divided result of the oxygen case. In such a case, a portion where oxygen does not actually exist (in this case, for example, a portion where a metallic element exists) shows bright contrast in an image observing oxygen distribution, and accordingly the oxygen distribution image has a small contrast difference to the metallic element portions.

In this case, processing of operating the element distribution image operated according to the two-window method using the electron beam intensity from the scattered electron beam detector 21 is selected, and operation is executed linking with the scanning coil 3. The operation executed here is to divide the element distribution image by the electron beam intensity from the scattered electron beam detector 21, or to divide the element distribution image by the square root of the electron beam intensity from the scattered electron beam detector 21, or to subtract the electron beam intensity obtained from the scattered electron beam detector 21 from the signal intensity expressing the element distribution image. An image obtained from the scattered electron beam detector is also called as a Z-contrast image, and the Z-contrast image depends on an atomic number of an element, and the contrast becomes brighter as the atomic number becomes larger. Therefore, by dividing the element distribution image obtained through the two-window method by the electron beam intensity from the scattered electron beam detector 21 or by the square root of the electron beam intensity from the scattered electron beam detector 21, or by subtracting the electron beam intensity obtained from the scattered electron beam detector 21 from the signal intensity expressing the element distribution image, the contrast in the metal portion becomes smaller than the contrast in the oxygen portion. By displaying the element distribution image as described above on the image display unit 25, the element distribution image of the element to be analyzed can be given with high contrast.

Figure 3A:
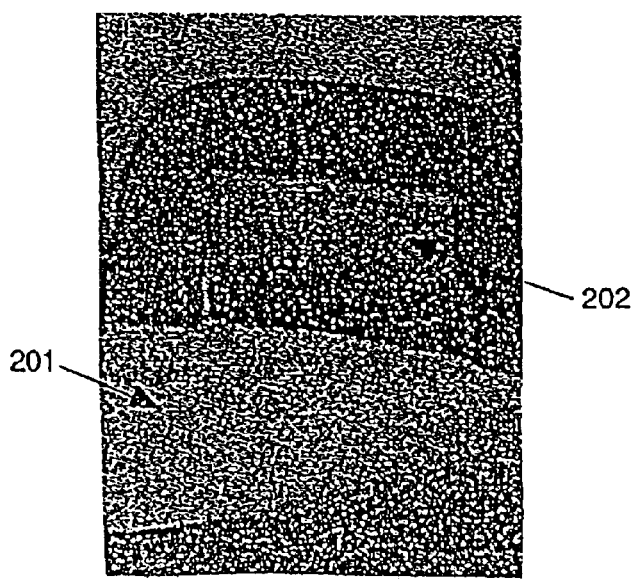
FIGS. 3(a) and (b) are STEM photographs showing an oxygen distribution image near a gate electrode of a semiconductor element and an oxygen distribution image obtained by dividing the oxygen distribution image by an electron beam intensity of a scattered electron beam detector.
Figure 3B:
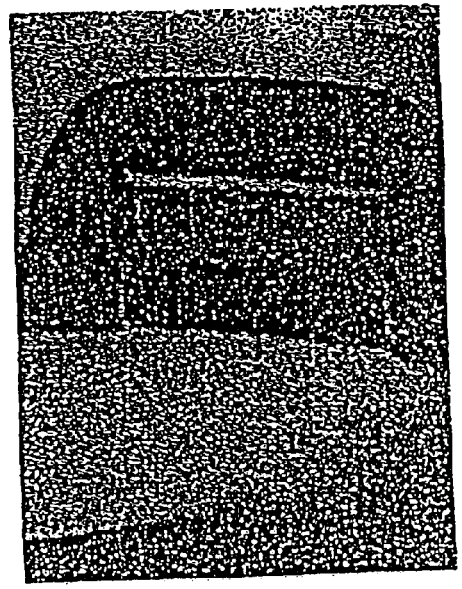

FIG. 3 is STEM photographs showing an oxygen distribution image near a gate electrode of a semiconductor device and an oxygen distribution image obtained by dividing the oxygen distribution image by an electron beam intensity of the scattered electron beam detector. The STEM photographs are results of observing a section near the electrode using tungsten as a metallic element for the electrode material. FIG. 3(a) is the element distribution image of oxygen observed by the two-window method. An element separation portion 201 is formed of a silicon oxide film, and the portion is in a bright contrast in the oxygen distribution image of FIG. 3(a). However, the gate electrode portion 202 is also bright. FIG. 3(b) is the result of dividing the oxygen distribution image of FIG. 3(a) by the electron beam intensity detected by the scattered electron beam detector at the same time of observing the oxygen distribution image. Although the contrast of the element separation portion 201 is bright similarly to that in FIG. 3(a), the contrast of the gate electrode portion 202 becomes dark. Accordingly, a high contrast oxygen distribution image excluded the effect of the metallic element can be obtained. The both of the photographs can be displayed in one screen on the image display unit 25 side-by-side. A plurality of image display units 25 may be used to separately display the photographs on the image display units one-by-one. By doing so, comparison between the both can be made clearer. Further, different from the above, both of the photographs may be colored and displayed side-by-side similarly to the above or overlapping with each other. By doing so, the display can be made clearer than the white-and-black display.

Figure 4A:
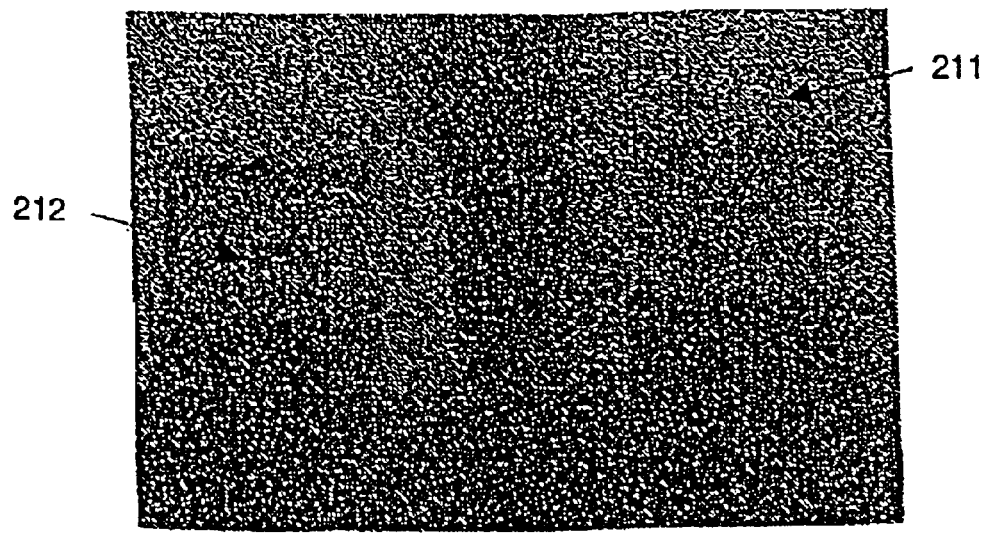
FIGS. 4(a) and (b) are STEM photographs showing a nitrogen distribution image near the electrode of a semiconductor element and a nitrogen distribution image obtained by dividing the nitrogen distribution image by an electron beam intensity of a scattered electron beam detector.
Figure 4B:
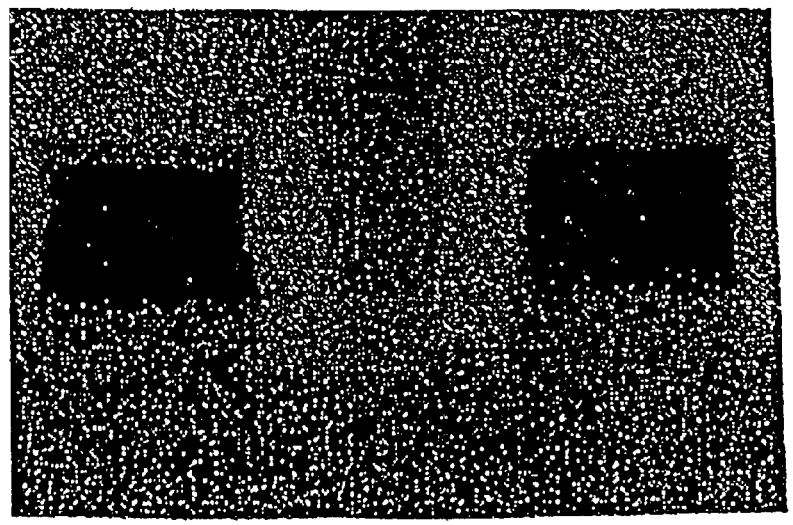

FIG. 4 is STEM photographs showing a nitrogen distribution image near the gate electrode of a semiconductor device and a nitrogen distribution image obtained by dividing the nitrogen distribution image by an electron beam intensity of a scattered electron beam detector. The STEM photographs are results of observing a section near the electrode using tungsten as a metallic element for the electrode material. FIG. 4(a) is the element distribution image of nitrogen observed by the two-window method. It can be understood that a silicon nitride film 211 is in a bright contrast in the nitrogen distribution image of FIG. 4(a). However, the electrode portion 212 is also bright. FIG. 4(b) is the result of dividing the nitrogen distribution image of FIG. 4(a) by the electron beam intensity detected by the scattered electron beam detector at the same time of observing the oxygen distribution image. Although the contrast of the silicon nitride film 211 is bright similarly to that in FIG. 4(a), the contrast of the electrode portion 212 becomes dark. Accordingly, a high contrast nitrogen distribution image excluded the effect of the metallic element can be obtained.

Similarly to FIG. 3, the both of the photographs of FIG. 4 can be displayed in one screen on the image display unit 25 side-by-side. A plurality of image display units 25 may be used to separately display the photographs on the image display units one-by-one. By doing so, comparison between the both can be made clearer. Further, different from the above, both of the photographs may be colored and displayed side-by-side similarly to the above or overlapping with each other. By doing so, the display can be made clearer than the white-and-black display.

FIG. 5 is STEM photographs showing an oxygen distribution image near the electrode of a semiconductor device and an oxygen distribution image obtained by subtracting the an electron beam intensity of a scattered electron beam detector from the oxygen distribution image the an electron beam intensity of a scattered electron beam detector. The STEM photographs are results of observing a section near the electrode using tungsten as a metallic element for the electrode material. FIG. 5(a) is the element distribution image of oxygen observed by the two-window method. It can be understood that a silicon oxide film 221 is in a bright contrast in the oxygen distribution image of FIG. 5(a). However, the electrode portion 222 is also bright. FIG. 5(b) is the result of subtracting the electron beam intensity detected by the scattered electron beam detector at the same time of observing the oxygen distribution image from the oxygen distribution image of FIG. 5(a). Although the contrast of the silicon oxide film 221 is bright similarly to that in FIG. 4(a), the contrast of the electrode portion 222 becomes dark. Accordingly, a high contrast oxygen distribution image excluded the effect of the metallic element can be obtained.

Figure 5A:
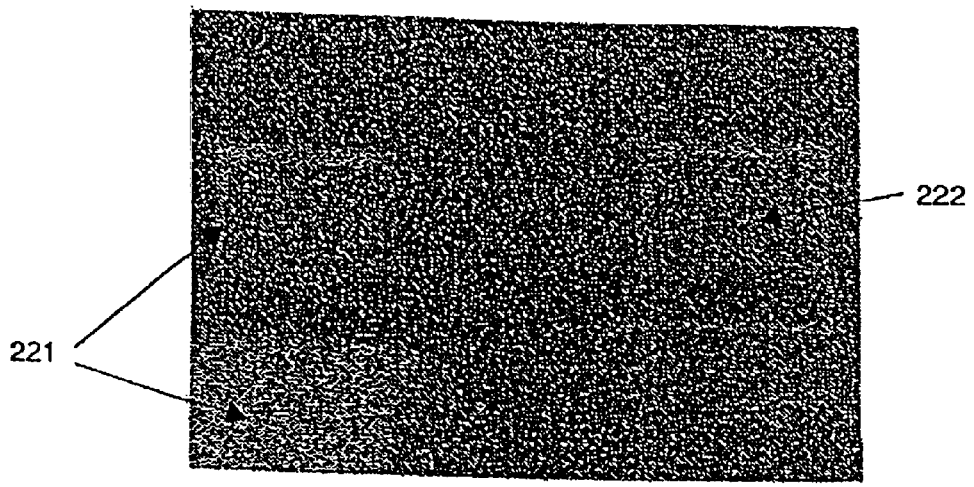
FIGS. 5(a) and (b) are STEM photographs showing an oxygen distribution image near the electrode of a semiconductor element and an oxygen distribution image obtained by subtracting the oxygen distribution image that was obtained by operating based on the an electron beam intensity of a scattered electron beam detector.
Figure 5B:
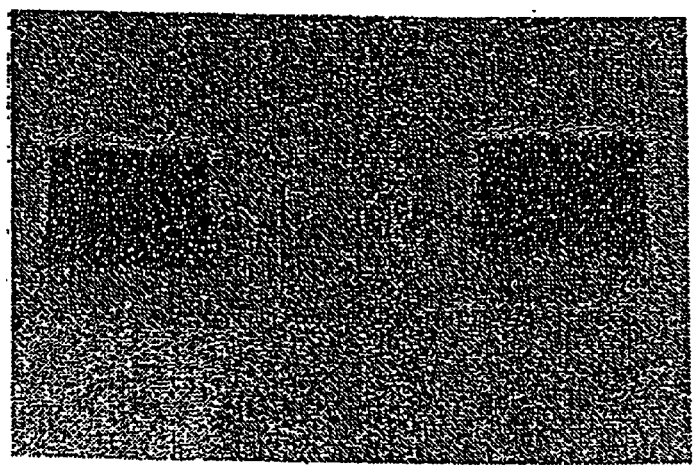
FIGS. 5(c) and (d) show a Z-contrast image and a superimposition display, respectively.
Figure 5C:
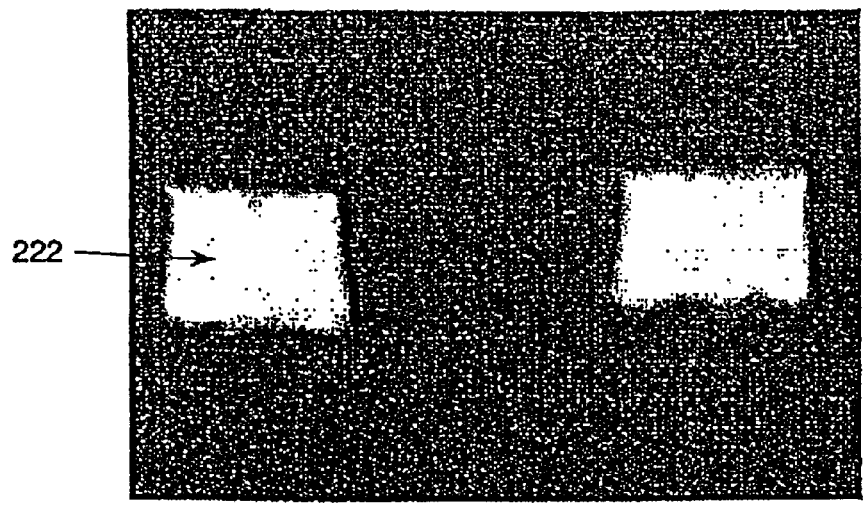

FIG. 5(c) is the Z-contrast image observed simultaneously with the element distribution image shown in FIG. 5(a). This Z-contrast image is displayed in red-based contrast gradation. In the displayed image of a semiconductor device, gate electrodes thereof brighten the most and other portions, silicon and oxidized silicon films, are darker than said electrode portions. The gate electrode materials in the semiconductor device under observation are tungsten (atomic number 74), silicon (14), and oxygen (8). Differences in these atomic numbers appear as differences in contrast gradation in the Z-contrast image. Displaying images of the element distribution and the Z-contrast with black and white gradation is useful for clearly discriminated indication of elements.

Figure 5D:
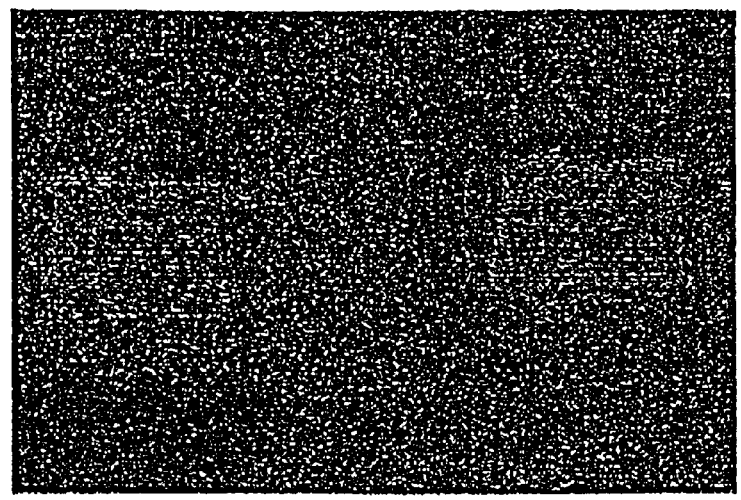

FIG. 5(d) shows the superimposition display using these two images by giving different colors to each of them. In the display, the oxygen distribution image is given blue-based gradation and the Z-contrast image red-based, which are then superimposed to be displayed. As shown in FIG. 5(d), the displayed element distribution image appears in bright blue for not only the oxidized silicon films but also for the tungsten electrode 222; other parts such as silicon portion however appear in a dark gradation. In the Z-contrast image, only the tungsten electrode 222 brightens in red but oxidized silicon film and silicon portion 223 dark. When images each of which color is given blue and red respectively are superimposed, the oxidized silicon film portion appears in bright blue, the silicon 223 portion in dark blue, and the tungsten electrode portion 222 reddish blue or bluish red. This superimposing technique in image displaying for analysis result of these kind realizes that a color-discriminated indication is practicable in displaying aspects of oxidized silicon films, the tungsten electrode 222, and silicon portion 223, which were not available by individual image display. In the specification, the red portion is rather bright and the blue portion is dark.

As stated above, a distribution image of nonferrous elements can be observed in high contrast by adding electron beam intensities of the ultimate image analysis and of the Z-contrast image.

Displaying images in other color tones than light and shade gives a clearly discriminating image of element distribution, particularly where two or more elements are involved.

Similarly to FIG. 3, the both of the photographs of FIG. 5 can be displayed in one screen on the image display unit 25 side-by-side. A plurality of image display units 25 may be used to separately display the photographs on the image display units one-by-one. By doing so, comparison between the both can be made clearer. Further, different from the above, both of the photographs may be colored and displayed side-by-side similarly to the above or overlapping with each other. By doing so, the display can be made clearer than the white-and-black display.

Further, the Z-contrast image and the element distribution image according to the two-window method can be captured at a time in synchronism with scanning of the electron beam. When the element distribution image according to the two-window method is corrected by the electron beam intensity detected by the scattered electron beam detector, a high accurate and high contrast element distribution image can be obtained because no displacement exists between the both images. Further, the element distribution image and the Z-contrast image can be observed at a time, and the results can be displayed on the image display unit 25 side-by-side. Particularly, by displaying the element distribution image and the Z-contrast image overlapping with each other, which position of a sample structural part an observed position in the element distribution image corresponds to can be easily determined at high resolution and with high accuracy.

Further, by operating an element distribution image operated according to a three-window method using the electron beam intensity detected by the scattered electron beam detector, a more contrast enhanced element distribution image can be obtained. The three-widow method is a method that in an electron energy loss spectrum, an electron beam intensity within an energy range including a core-loss edge due to the excitation of inner-shell electron in an observed element is subtracted by an electron beam intensity of the background portion of the electron energy loss spectrum, and the result is displayed as the element distribution image.

Further, there are provided a plurality of scattered electron beam detectors, those have different radius, for detecting scattered electrons, and at least one of them is a scattered electron beam detector specifically designed for detecting heavy elements such as metals and arranged so as to selectively detect heavy elements having atomic number larger than that of light elements such as oxygen and nitrogen. An element distribution image of oxygen or the like is observed by the two-window method and at the same time scattered electrons are detected by the scattered electron beam detector for heavy element, and the result operated by the two-window method is divided by the electron beam intensity detected by the scattered electron beam detector for heavy element. The element distribution image operated as described above is an image in which only the heavy element portions are selectively in dark contrast. Accordingly, a light element distribution image excluded the effect of the metallic element can be obtained.

As described in the present embodiment, it is possible to obtain an ultimate analyzer capable of observing and displaying an element distribution image and a Z-contrast image at the same time in real time during scanning the electron beam and also capable of observing an element distribution image corrected by the Z-contrast image; and a scanning transmission electron microscope comprising the ultimate analyzer; and a method of analyzing elements using the ultimate analyzer.

According to the present invention, a light element distribution image excluded the effect of the heavy element such as a heavy metal can be obtained by combining the ultimate analyzer and the scanning transmission electron microscope and correcting an element distribution image using the electron beam intensity detected by the scattered electron beam detector. Therefore, in the present invention, a light element distribution image can be observed in high contrast, at high resolution and with high accuracy.

What is claimed as new and desired to be protected by Letters Patent of the United States is:

1. An ultimate analyzer comprising:
   a scattered electron beam detector for detecting an electron beam scattered by an object to be analyzed;
   an electron spectrometer for energy dispersing an electron beam transmitted through said object to be analyzed;
   an electron beam detector for detecting said dispersed electron beam; and
   a control unit for analyzing elements of said object to be analyzed based on a computed output signal obtained either through adding or subtracting operation applied between an output signal, or a calculation result obtained based on said output signal, of the election beam detected by said electron beam detector and an output signal of the scattered electron beam detected by said scattered electron beam detector or through dividing operation applied to said output signal or said calculation result of said electron beam using the square root of said output signal of said scattered electron beam as the divisor.

2. An ultimate analyzer comprising:
   a scattered electron beam detector for detecting an electron beam scattered by an object to be analyzed;
   an electron spectrometer for energy dispersing an electron beam transmitted through said object to be analyzed;
   an electron beam detector for detecting said dispersed electron beam;
   an image display unit for displaying an element distribution image of said object to be analyzed obtained through computation based on an output signal of the electron beam detected by said electron beam detector and an element distribution image of said object to be analyzed obtained through computation based on an output signal of the electron beam detected by said scattered electron beam detector; and
   a computing unit either for adding or subtracting operation between the intensity of said dispersed electron beam, or a calculation result obtained based on said intensity, and the intensity of said scattered electron beam or for dividing operation to said intensity of transmission electron beam, or said calculation result, using the square root of said intensity of scattered electron beam as the divisor.

3. An ultimate analyzer comprising:
   a scattered electron beam detector for detecting an electron beam scattered by an object to be analyzed;
   an electron spectrometer for energy dispersing an electron beam transmitted through said object to be analyzed;
   an electron beam detector for detecting said dispersed electron beam;
   any one of an image display unit for displaying line profiles of an element of said object to be analyzed obtained from an analysis result output from a control unit for operating the element of said object to be analyzed based on an output signal of the electron beam detected by said electron beam detector and an analysis result output from said control unit for analyzing the element of said object to be analyzed based on an output signal of the electron beam detected by said scattered electron beam detector, and an image display for displaying a distribution image of said element, and an image display unit for displaying said distribution image of said element and a distribution image of said element based on the output signal of the electron beam detected by said scattered electron beam detector at a time with two image planes side-by-side or sequentially one-image planes or overlapping two image planes with each other; and
   a computing unit either for adding or subtracting operation between the intensity of said dispersed electron beam, or a calculation result obtained based on said intensity, and the intensity of said scattered electron beam or for dividing operation to said intensity of transmission electron beam, or said calculation result, using the square root of said intensity of scattered electron beam as the divisor.

4. An ultimate analyzer according to any one of claims 1 to 3, which comprises an accelerator for accelerating the electron beam transmitted through said object to be analyzed, wherein said control unit controls said accelerator so that said transmitted electron beam corresponding to the element of said object to be analyzed may be incident to a fixed position of said electron beam detector, and executes operation processing for analyzing the element of said object to be analyzed based on output signals of the electron beam in a plurality of energy ranges detected by said electron beam detector.

5. An ultimate analyzer according to any one of claims 1 to 3, wherein said control unit comprises a memory part for pre-storing a value of acceleration voltage for accelerating said transmitted electron beam and an energy range of said transmitted electron beam for detecting the element of said object to be analyzed; and an operation part for operating analysis of the element of said object to be analyzed based on an output signal of the electron beam in said pre-stored energy range, or an intensity of said electron beam and the output signal of the electron beam detected by said scattered electron beam detector.

6. An ultimate analyzer according to any one of claims 1 to 3, which analyzes the element of said object to be analyzed based on output signals of the electron beam within a plurality of energy ranges among intensities of said dispersed electron beam detected by said electron beam detector or based on the output signal of said electron beam and the output signal of the electron beam detected by the scattered electron beam detector, and comprises any one of an image display unit for displaying a line profile of an element of said object to be analyzed based on the output signal of said electron beam relating to said analyzed element and an electron beam irradiated position in said object to be analyzed; and an image display unit for displaying a distribution image of said element; and an image display unit for displaying said distribution image of said element and a distribution image of said element based on the output signal of the electron beam detected by said scattered electron beam detector at a time with two image planes side-by-side or sequentially one-image planes or overlapping two image planes with each other.

7. An ultimate analyzer, according to claim 5, wherein said memory part stores correcting data for removing an individual influence specific to said electron beam detector for detecting said transmitted electron beam, and said operating part corrects the output signal of said detected electron beam based on said correcting data.

8. An ultimate analyzer according to claim 5, wherein a first energy range of an energy range including a core-loss edge expressed by a transmitted electron energy loss spectrum relating to the element of said object to be analyzed arid a second energy range of an energy range higher than the core loss energy are pre-stored in said memory part, said control unit controls so as to an output signal of a first electron beam detected by an electron beam detecting portion corresponding to said first energy range and an output signal of a second electron beam detected by an electron beam detecting portion corresponding to said second energy range based on said first energy range and said second energy range, and said operating part execute operation processing of the output signal of said first electron beam and the output signal of said second electron beam, and executes operation processing of analyzing the element of said object to be analyzed based on relationship between said operation processed result and the output signal of the electron beam detected by said scattered electron beam detector.

9. An ultimate analyzer according to claim 8, which comprises an image display unit for displaying said operation processed result or an operation processed result based on relationship between said operation processed result and the output signal of the electron beam detected by said scattered electron beam detector; and the result based on the output signal of the electron beam detected by said scattered electron beam detector at a time with two image planes side-by-side or sequentially one-image planes or overlapping two image planes with each other.

10. An ultimate analyzer according to any one of claims 1 to 3, which comprises a plurality of said electron beam detectors for the transmitted electron beam or a plurality of said scattered electron beam detectors.

11. An scanning transmission electron microscope comprising an electron beam source; an electron beam scanning coil for scanning an electron beam emitted from said electron beam source; an upper objective lens for irradiating the emitted electron beam passed through said coil on a sample; a lower objective lens for condensing the electron beam coming out from said sample; a scattered electron detector for detecting a scattered electron beam among electron beams transmitted through the sample; a phase contrast detector for detecting a phase of an electron beam traveling straight among the electron beams; a lens for focusing the irradiating electron beam; a lens for magnifying the electron beam coming out from an electron spectrometer; and an electron beam detector for detecting the electron beam coming out from said electron spectrometer, which further comprises an ultimate analyzer for analyzing elements of said sample.

12. A scanning transmission electron microscope, comprising an electron beam source; an electron beam scanning coil for scanning an electron beam emitted from said electron beam source; an upper objective lens for irradiating the emitted electron beam passed through said coil on a sample; a lower objective lens for condensing the electron beam coming out from said sample; a scattered electron detector for detecting a scattered electron beam among electron beams transmitted through the sample; a phase contrast detector for detecting a phase of an electron beam traveling straight among the electron beams transmitted through the sample; a lens for focusing the irradiating electron beam; a lens for magnifying the electron beam coming out from an electron spectrometer; and an electron beam detector for detecting the electron beam coming out from said electron spectrometer, which further comprises an ultimate analyzer for analyzing elements of said sample, wherein said ultimate analyzer is one of the ultimate analyzer according to claims 1 to 3.

13. An ultimate analysis method comprising the steps of detecting an electron beam transmitted through an object to be analyzed; and analyzing an element of said object to be analyzed based on an output signal of the detected electron beam,
    wherein an intensity of said output signal is corrected by an output signal obtained either from adding or subtracting operation using the intensity of an electron beam scattered by said object to be analyzed or from dividing operation using the square root of the intensity of said scattered electron beam as the divisor.

14. An ultimate analysis method comprising the steps of
    detecting an electron beam transmitted through an object to be analyzed;
    detecting an element of said object to be analyzed based on an output signal of the detected electron beam; and
    displaying an image of said ultimate analysis on a screen,
    wherein the intensity of said electron beam or the result of calculation obtained based on said intensity of electron beam of said image of said ultimate analysis is corrected by an output signal obtained either from adding or subtracting operation using the intensity of an electron beam scattered by said object to be analyzed or from dividing operation using the square root of the intensity of said scattered electron beam as the divisor.

15. An ultimate analysis method comprising the step of correcting an image of an ultimate analysis by an output signal obtained either from adding or subtracting operation using the intensity of an electron beam scattered by an object to be analyzed or from dividing operation using the square root of the intensity of said scattered electron beam as the divisor,
    said image of said ultimate analysis being obtained from an operation based on an energy range of core-loss edge expressed an electron energy loss spectrum due to inner-shell electron excitation by an electron beam transmitted through said object to be analyzed and an energy range just before said core-loss edge.

16. An ultimate analysis method comprising the step of analyzing an element of an object to be analyzed based on an energy range of core-loss edge expressed in an electron energy loss spectrum due to inner-shell electron excitation by electrons transmitted through said object to be analyzed and an energy range just before said core-loss edge, wherein the intensity of an electron beam or the result of calculation obtained based on said intensity in said analysis is corrected by an output signal obtained either from adding or subtracting operation using the intensity of an electron beam scattered by said object to be analyzed or from dividing operation using the square root of the intensity of said scattered electron beam as the divisor.

17. An ultimate analysis method comprising the step of displaying an ultimate analysis image and a Z contrast image on a screen, said ultimate analysis image being obtained from an operation based on an energy range of core-loss edge expressed in an electron energy loss spectrum due to inner-shell electron excitation by electrons transmitted through said object to be analyzed and an energy range just before said core-loss edge, said Z-contrast image being obtained from operation based on an intensity of an electron beam scattered by said object to be analyzed.

18. An ultimate analysis method comprising the steps of detecting an electron beam transmitted through an object to be analyzed; analyzing an element of said object to be analyzed based on an output signal of the detected electron beam; and displaying an image of said ultimate analysis on a screen, wherein said image of said ultimate analysis is displayed on the screen together with a Z-contrast image obtained from operation based on an intensity of an electron beam scattered by said object to be analyzed.

19. An ultimate analysis method comprising the steps of detecting an electron beam transmitted through an object to be analyzed; analyzing an element of said object to be analyzed based on an output signal of the detected electron beam; and displaying an image of said ultimate analysis on a screen, wherein the intensity of said electron beam or the result of calculation obtained based on said intensity in said image of said ultimate analysis is displayed on the screen by being corrected either by adding or subtracting operation applied to the intensity of an electron beam or to the result of calculation obtained based on said intensity in a Z-contrast image obtained from operation based on an intensity of an electron beam scattered by said object to be analyzed or by dividing operation using the square root of said output signal as the divisor.

* * * * *